United States Patent [19]

Lerman

[11] Patent Number: 4,538,597
[45] Date of Patent: Sep. 3, 1985

[54] CERVICAL COLLAR

[76] Inventor: Max Lerman, 1950 Carla Ridge, Beverly Hills, Calif. 90210

[21] Appl. No.: 554,351

[22] Filed: Nov. 22, 1983

Related U.S. Application Data

[63] Continuation-in-part of Ser. No. 511,841, Jul. 8, 1983.

[51] Int. Cl.³ .............................................. A61F 5/01
[52] U.S. Cl. ................................. 128/75; 128/87 B; 128/DIG. 23
[58] Field of Search ................ 128/75, DIG. 23, 87 B

[56] References Cited

U.S. PATENT DOCUMENTS

| | | | |
|---|---|---|---|
| 3,042,027 | 7/1962 | Monfardini | 128/DIG. 23 |
| 3,756,226 | 9/1973 | Calabrese et al. | 128/75 |
| 3,916,885 | 11/1975 | Gaylord, Jr. | 128/DIG. 23 |
| 4,099,523 | 7/1978 | Lowrey | 128/75 |

Primary Examiner—John D. Yasko
Attorney, Agent, or Firm—Christie, Parker & Hale

[57] ABSTRACT

A cervical collar comprises front and rear halves for resting on the shoulders and extending around the neck to support the chin and rear of a patient's head. Each half comprises a thin, semi-rigid shell molded from a plastic material such as polyethylene. The front half preferably comprises a self-supporting shell preformed as a single piece of a thin, semi-rigid material shaped to conform to the anatomical contour of the underside of the chin and lower jaw, the front portion of the neck, and the upper chest region. The length of the neck region of the shell is reinforced for increasing its stiffness to resist without collapse the downward forces on the chin and lower jaw-supporting section of the shell normally encountered during use. A resilient open cell containing material provides padding for the inside face of the shell. The rear half of the collar comprises a similar thin semi-rigid shell with an open cell containing material on its inside face. Flexible straps with Velcro fasteners on the rear half are attached to cooperating Velcro fasteners on the neck region of the front half of the collar. In one embodiment, the neck region of the collar is reinforced by an elongated embossed region extending lengthwise across the neck region of the shell for increasing the structural stiffness of the neck region without either increasing the wall thickness of the shell or adding separate reinforcing materials.

9 Claims, 6 Drawing Figures

CERVICAL COLLAR

CROSS REFERENCE TO RELATED APPLICATION

This is a continuation-in-part of my application Ser. No. 511,841, filed July 8, 1983.

BACKGROUND OF THE INVENTION

1. Field of the Invention

This invention relates to an improved cervical collar.

2. Description of Prior Art

In the past, there have been different types of cervical collars used on patients who have suffered neck injuries. The cervical collar provides rigid support for the cervical vertebrae to immobilize the vertebrae while relieving pressures on cervical nerves by supporting the head and preventing undue pressures from being applied to the neck. A cervical collar should maintain front-to-back stability of the patient's head in addition to preventing rotation of the head.

It is important for a cervical collar to be comfortable, since the collar may be worn continuously for a long period of time.

A popular cervical collar known as the Philadephia collar is disclosed in U.S. Pat. No. 3,756,226 to Calabrese et al. The Philadelphia collar is formed in two halves and each half is made from a closed cell polymeric foam material such as polyethylene or polyurethane. The closed cell material is desirable because it can be formed into the desired shape in a die or mold. The foam material makes the collar reasonably light in weight. However, the collar is not comfortable when worn continuously for long periods of time. The closed cell material does not "breathe" and when the closed cell collar is worn for long periods, it can cause the patient to perspire which can lead to heat rashes or other skin problems. Closed cell materials do not "breathe" in the sense that they are resistant to air circulation through them and they do not absorb fluids. Large air holes in the front and rear halves of the Philadelphia collar provide some air circulation to the skin, but the closed cell material still resists proper air circulation, fluid absorption and heat dissipation that would otherwise make the collar comfortable during prolonged use.

The present invention provides a cervical collar which is more comfortable to wear for long periods than the Philadelphia collar. The cervical collar of this invention is made, in part, from an open cell foam material which breathes during use and therefore does not create skin problems or other discomfort when the collar is worn for long periods of time.

Open cell materials are not capable of being molded to the desired anatomical shape as are closed cell materials. However, the cervical collar of this invention is made so that the open cell material can be supported in the desired anatomical shape to provide the comfort not provided by a closed cell material; and yet the cervical collar of this invention provides the desired comfort while also providing the required stability of support for the patient wearing the collar.

SUMMARY OF THE INVENTION

One embodiment of the cervical collar has front and rear halves, each being generally U-shaped and being adapted for attachment to each other for supporting the chin region and the back of the patient's head. The invention is directed principally to the front half of the cervical collar which includes a preformed semi-rigid, one-piece shell in a three-dimensional anatomical shape that conforms to the underside of the chin region, the front portion of the neck, and the upper chest region of the patient. The inside face of the shell has a resilient open cell layer on the side for contact with those anatomical regions to which the shape of the preformed shell conforms. A reinforcing section extends across the front of the shell beneath the chin-supporting region of the shell. The reinforcing section adds stiffness to the shell so that the shell in and of itself has sufficient rigidity to support the patient's chin region without the shell collapsing when the collar is in use.

In one form of the invention, the reinforcing section is an embossed region of the shell that extends across the front of the neck region of the shell. The embossed region provides stiffness to the shell below the chin-supporting region of the shell to resist downward forces on the chin-supporting region incurred during normal use of the cervical collar. This resistance to downward forces allows the chin-supporting region of the shell and the lower neck region and the region covering the upper chest area to remain stable during normal use.

The semi-rigid preformed shell facilitates use of the open cell material for padding, which makes the collar comfortable for the patient during long periods of use. Skin rashes and other problems created by prolonged use of a collar made from a closed-cell material are alleviated.

These and other aspects of the invention will be more fully understood by referring to the following detailed description and the accompanying drawings.

DRAWINGS

DETAILED DESCRIPTION

Figure 1:
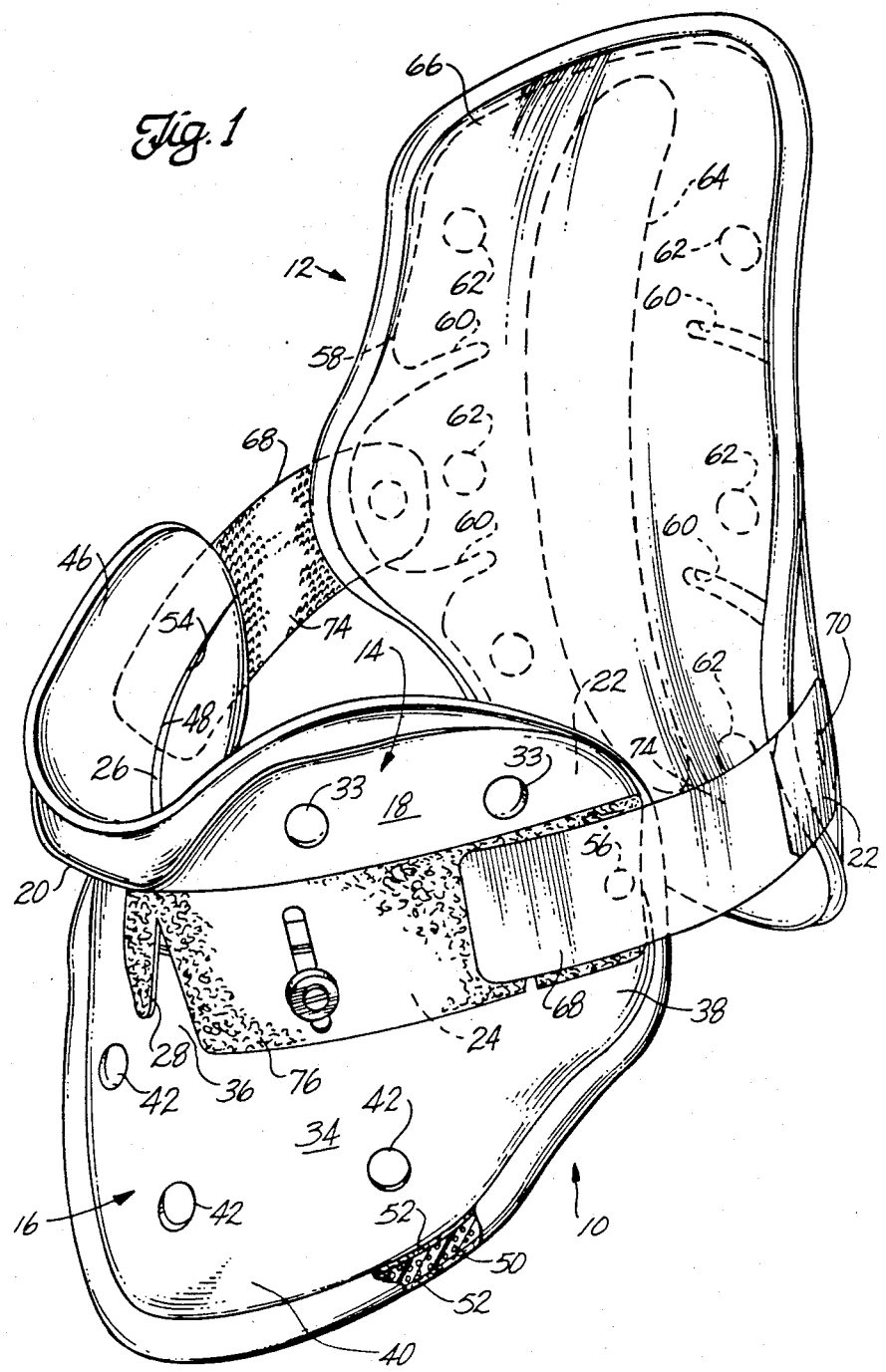
FIG. 1 is a perspective view showing front and rear halves of an adjustable cervical collar according to principles of this invention.
Figure 2:
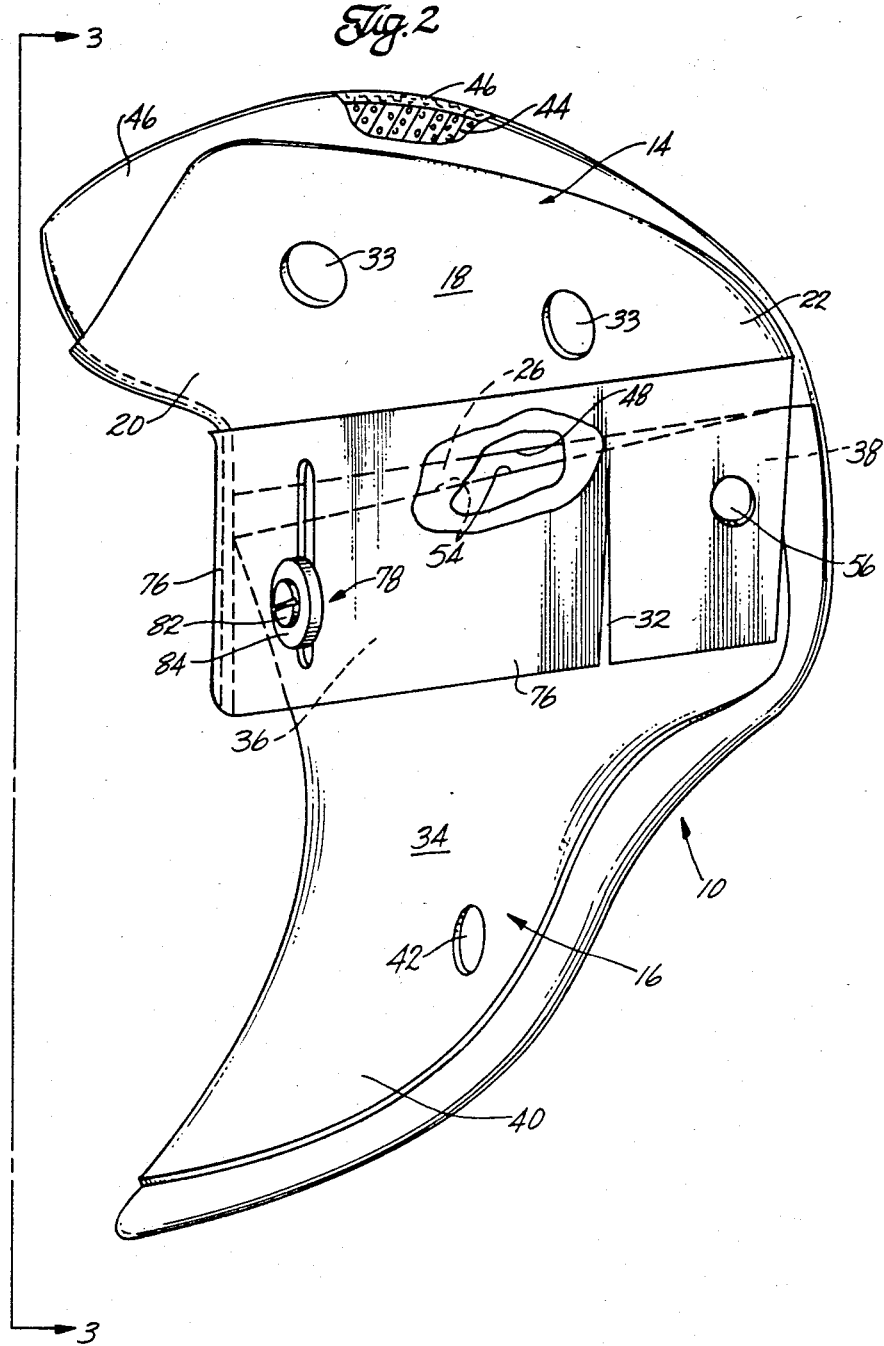
FIG. 2 is a side elevation view, partly in cross section and partly broken away, showing the front half of the adjustable cervical collar.
Figure 3:
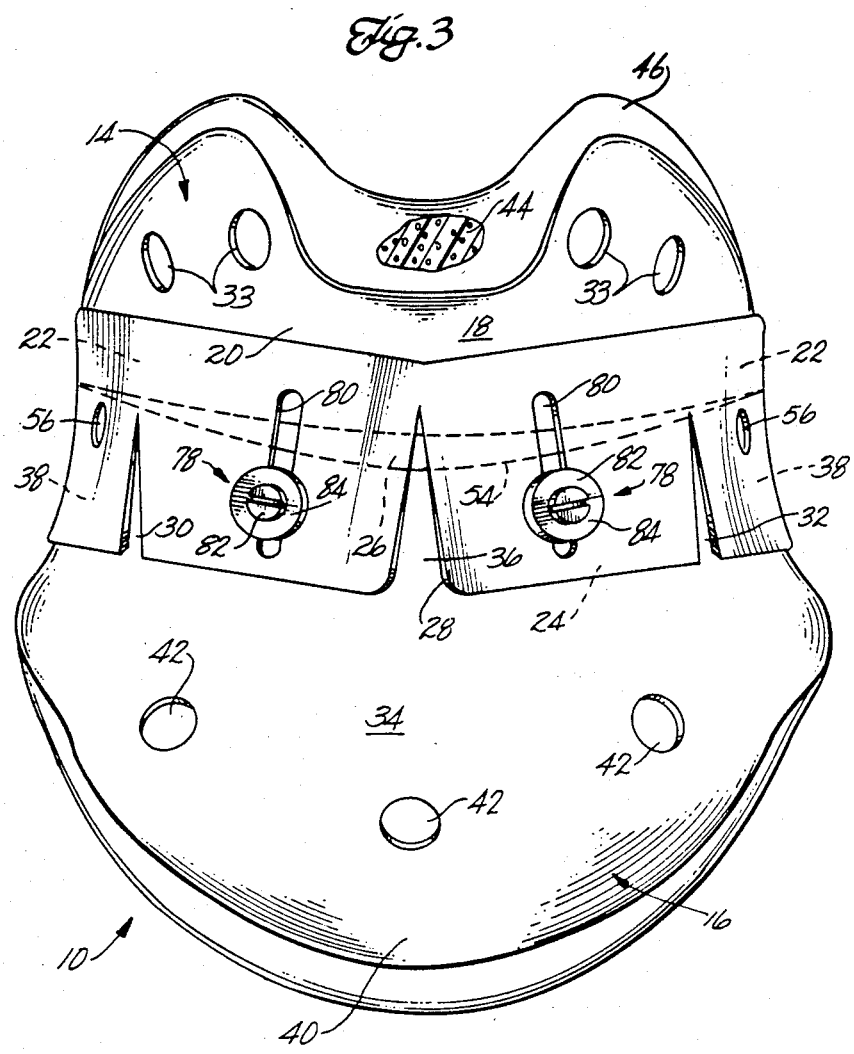
FIG. 3 is a front elevation view, partly broken away, taken on line 3—3 of FIG. 2.
Figure 4:
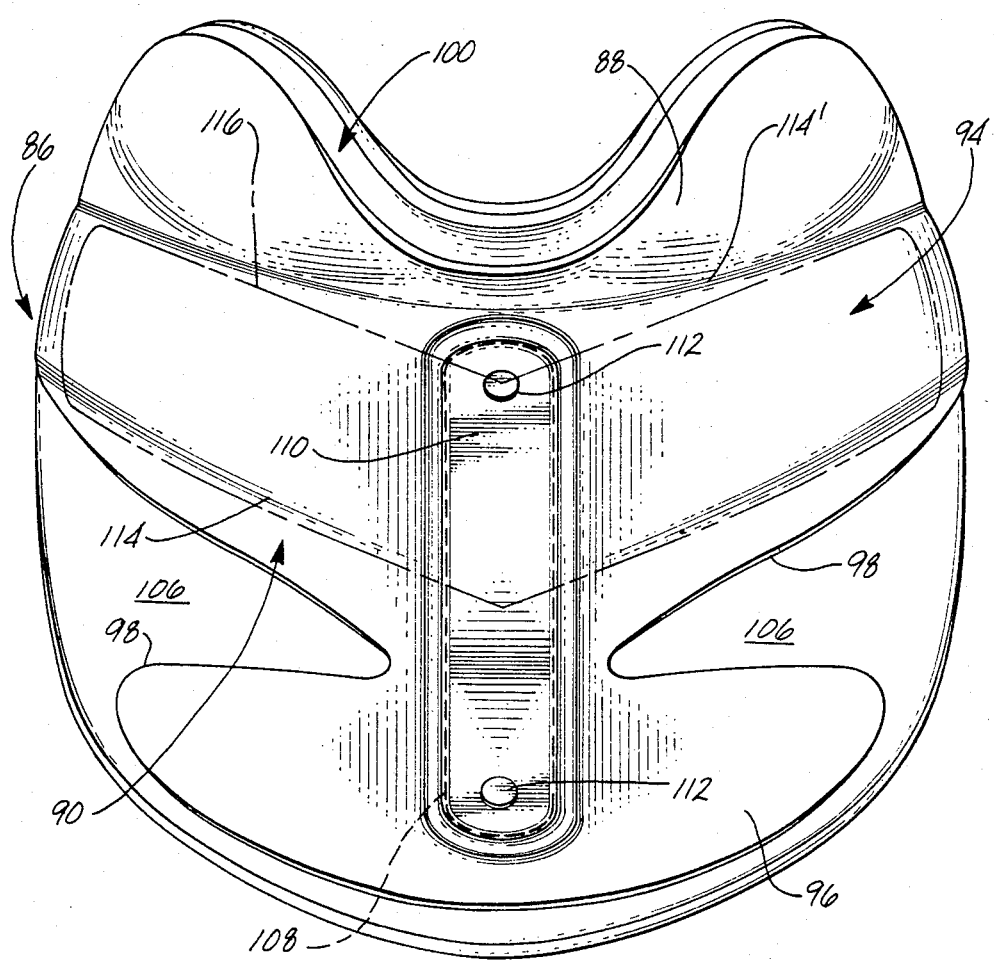
FIG. 4 is a front elevation view, partly broken away, showing the front half of a fixed cervical collar according to principles of this invention.
Figure 5:
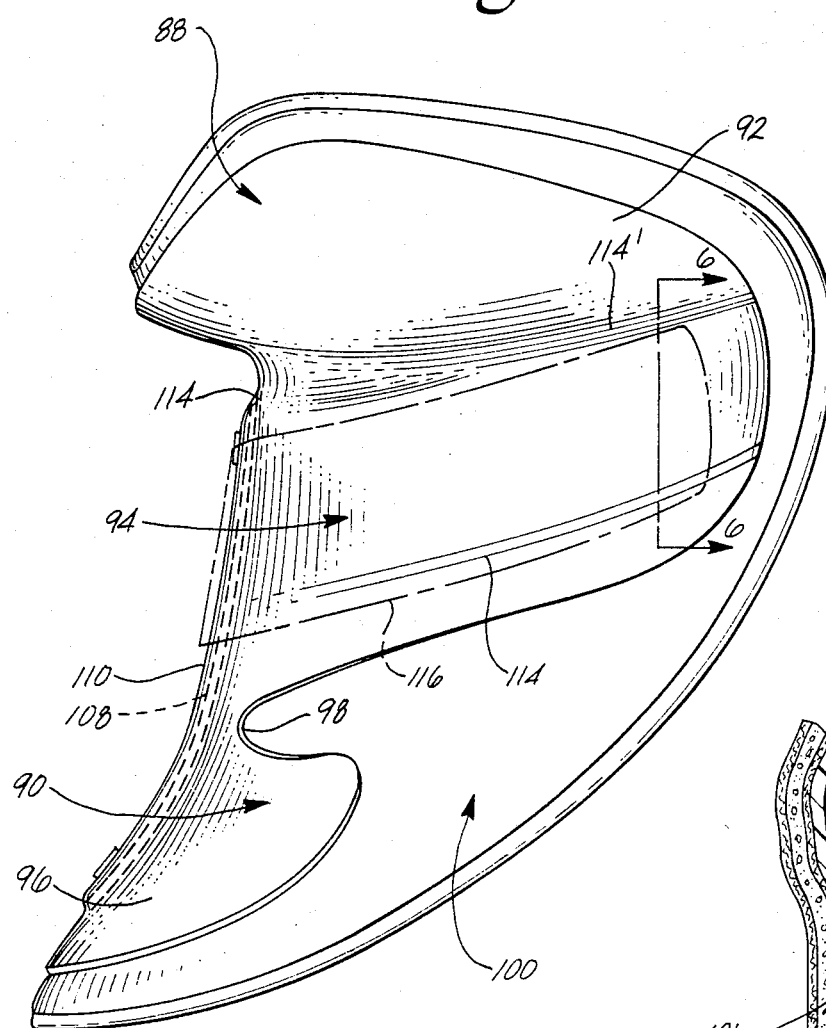
FIG. 5 is a side elevation view taken on line 5—5 of FIG. 4.

FIGS. 1 through 3 show an adjustable cervical collar according to principles of this invention. FIGS. 4 and 5 show a fixed cervical collar which is an alternate embodiment of the invention. The adjustable collar of FIGS. 1 through 3 includes a generally U-shaped front half 10 for supporting the chin region of a patient and a generally U-shaped rear half 12 for supporting the rear or occipital portion of the patient's head. The front half 10 of the collar is in the form of a shell which is split into upper and lower sections comprising a chin-supporting upper section 14 and a lower section 16 that fits around the lower front portion of the patient's neck and rests on the front of the collarbone and the upper chest region of the patient.

The chin-supporting upper section 14 is made from a semi-rigid self-supporting shell 18 of a material preformed to conform to an anatomical shape that can support the underside of the chin region of the patient. The upper shell 18 is preferably made from a thin sheet of polyethylene that is sufficiently flexible to be vacuum-formed into the desired shape and which remains reasonably flexible after shaping. The chin-supporting upper shell 18 has an elongated upwardly opening U-shaped portion 20 for extending under and along the sides of the patient's chin. The upper portion of the shell 18 extends to rear portions 22 for overlying rear portions of the patient's lower jaw. The lower portion of the upper shell 18 formed as a generally U-shaped reinforcing bridge member 24 (it is U-shaped when viewed from above) which overlaps a narrow slot 26 formed as a split between the upper and lower sections of the collar front half. The bridge member 24 is an integral part of the upper shell 18 and extends below the upper front and rear portions 20 and 22 in a manner akin to a generally vertical skirt. The bridge member is reasonably flexible laterally, but is substantially stiff longitudinally, i.e., it resists edgewise forces during use without flexing. The upper shell 18 is formed so that the bridge member extends generally normal to the chin and jaw supporting upper portions of the shell, so that the edgewise stiffness of the bridge member provides stiff support resisting downward forces on the chin and jaw-supporting portions of the upper shell. The U-shaped bridge member is partially split by a central groove 28 in its front lower edge. This groove permits the U-shaped member to flex lengthwise and laterally when the upper section 14 is moved relative to the lower section 16. Added flexibility can be provided by additional grooves 30 and 32 near the rear portions of the U-shaped reinforcing member. Air holes 33 are formed in the upper shell.

The lower section 16 of the collar front half is made from a thin, semi-rigid shell 34 that has been preformed to conform to the contour of the lower front portion of the patient's neck and the front portion of the collarbone and upper central portion of the patient's chest region. The lower shell 34 is preferably made from the same material as the upper shell 18. It is preferably vacuum-formed from a thin, flexible but self-supporting sheet of material such as polyethylene. The lower shell 34 has a U-shaped (when viewed from above) upper portion 36 for conforming to the shape of the lower portion of the patient's neck. This portion of the shell extends rearwardly along both sides of the patient's neck to end regions 38 below the end portions of the patient's lower jaw. The lower shell 34 flares outwardly to the sides and forwardly and downwardly below the U-shaped upper portion 36 to form a generally U-shaped (when viewed from the front) lower portion 40 shaped to conform to the front portion of the collarbone and the upper central region of the patient's chest. Air holes 42 are formed in the lower shell 34.

A layer of padding covers the inside face of the upper shell 18. The layer preferably comprises an internal layer 44 of an open cell resilient plastic foam material such as polyurethane foam. The open cell foam material is used because the open cell material is capable of "breathing", i.e., it allows air circulation through the cells and absorbs moisture, as opposed to a closed cell material which does not breathe appreciably and which does not absorb fluids to any significant extent.

The open cell foam layer is enclosed within an outer layer 46 of a soft flexible fabric that is also capable of breathing and is comfortable when in direct contact with the skin for long periods of time. A preferred outer layer material is velour. The enclosure formed by the velour is preferably made by overlaying two pieces of velour on opposite faces of the open cell foam layer and then fastening the overlying layers of velour by stitching around the entire outer perimeter of the foam layer. The resulting padding is then affixed to the inside face of the upper shell by a suitable adhesive. The padding covers the chin-supporting portion of the upper shell 18 and terminates at a lower edge 48 which extends across the lower portion of the U-shaped chin-supporting portion of the upper shell, leaving the inside face of the bridge member free of such padding.

A similar layer of padding covers the inside face of the lower shell 34. The padding on the lower shell preferably comprises a similar internal layer 50 of a resilient open cell plastic foam material such as polyurethane foam enclosed within outer layers 52 of velour. The padding that covers the inside face of the lower shell terminates at an upper edge 54 adjacent the lower edge 48 of padding on the upper shell.

The upper and lower sections 14, 16 of the collar front half are hinged to each other so that one section is movable toward or away from the other section. A pair of rivets 56 pivot the rear lower jaw regions of the upper and lower sections 14, 16 to each other. The two sections are secured so that the elongated bridge member 24 of the upper shell 18 overlaps the upper portion 36 of the lower shell 34. The rivets attach the opposite rear portions of the bridge member 24 to the upper rear portions 38 of the lower shell. The bridge member thus forms a U-shaped (when viewed from above) piece that overlies the U-shaped upper portion 36 of the lower shell continuously from the rear lower jaw region on one side, around the front of the patient's neck, to the rear lower jaw region on the other side of the patient. The hinging of the upper and lower sections allows the two sections to pivot through an angle about a transverse axis through the rivets. This allows the upper and lower sections to pivot through infinitely adjustable angular positions relative to one another, which either widens or closes the split 26 between the two sections. The two sections pivot between a closed position, in which the bridge member has its maximum overlap on the upper portion 36 of the lower shell, to a fully open position in which the overlap of the bridge member is at its minimum. In the closed position, the confronting lower and upper edges 48, 54 of the padding are in contact with each other. As the two sections pivot apart toward the fully open position, the tapered gap 26 between the edges of the padding is widened. The position of the cervical collar shown in FIGS. 1 through 3 is near the fully open position of the collar.

The rear half 12 of the collar includes a semi-rigid shell 58 preferably made from a thin self-supporting but flexible plastic piece such as polyethylene. The shell 58 is shaped to conform to the slightly U-shaped shallow curvature of the head from the occipital region down along the rear of the neck to the upper shoulder region. Narrow slots 60 are formed in opposite sides of the rear shell 58 to add flexibility. Air holes 62 also are formed in the shell. A metal reinforcing bar 64 extends along the vertical centerline of the rear shell to add rigidity. The reinforcing bar is made of a malleable metal such as aluminum so that it can be shaped to conform to the curvature of the patient's rear neck region. A layer of resilient padding 66 covers the inside face of the shell 58. The padding is made from a material similar to the padding that covers the inside faces of the upper and lower sections 14 and 16 of the front half fo the collar, i.e., a resilient open cell plastic foam material such as polyethylene internally within outer layers of velour. The padding is affixed to the inside face of the shell 58 by a suitable adhesive.

A pair of flexible straps 68 are affixed to opposite sides of the rear half 12 of the collar. The flexible straps are preferably affixed by rivets 70 extending through vinyl reinforcing pieces 72. The flexible straps are preferably made of a strong flexible material such as nylon. The inside faces of the flexible straps have a thistle cloth fastener material 74, preferably a layer of Velcro hook-type material. In use, the straps 68 extend toward the U-shaped bridge member 24 on the front half 10 of the collar so that the straps can overlie the bridge member. A layer 76 of a thistle cloth fastener material is affixed to the front face of the bridge member 24. Preferably, the fastener material 76 is Velcro pile type material. In use, the front and rear halves 10 and 12 of the cervical collar can be attached to one another by overlapping the free ends of the straps on the bridge member and attaching the cooperating Velcro surfaces to hold the front and rear halves of the collar in place.

A pair of fastening and guide means 78 hold the upper and lower sections 14 and 16 of the collar front half in the desired angular position and guide the angular travel between the two sections. The fastening and guide means include a pair of laterally shaped apart narrow, elongated right and left slots 80 formed in the front central portion of the bridge member 24. The right and left slots are generally parallel to one another and extend generally vertically from near the chin supporting portion of the upper shell downwardly toward the bottom edge of the bridge member. During use, the two slots extend generally vertically over the right and left front central portions of the patient's neck. Separate posts (not shown) extend through the guide slots 80. Each post is preferably formed by a rivet affixed to the underside of the U-shaped upper region 36 of the lower shell. Each rivet has an internally threaded shank which extends through a corresponding guide slot 80. A pair of screws 82, each carrying a washer 84, are threaded into the internally threaded shanks of the rivets that extend through the slots 80. The screws can be loosened to allow the upper and lower sections 12 and 14 to pivot through an angle to the desired angular position between them. The screws then can be tightened to apply force to the front face of the bridge member through the washers for holding the two sections in the desired angular position. The shank portions of the rivets act as posts to cooperate with the guide slots to guide angular travel between the upper and lower sections.

The cervical collar is used by placing the upper section 14 of the collar front half 10 under the patient's chin and supporting it by the lower section 16 which rests on the patient's collarbone region and the upper central portion of the patient's chest region. The upper and lower sections 14 and 16 are adjusted to the patient's neck size by adjusting the angle between the upper and lower sections. The screws 82 are loosened to pivot the two sections relative to one another to the desired angular setting. The screws are tightened to hold the upper and lower sections in the desired position. The rear half 12 of the collar is then placed against the rear occipital region of the patient and the lower portion of this section is supported at the rear upper central portion of the patient's shoulder region. The flexible straps 68 are then extended forward around opposite sides of the patient's neck and are attached to the Velcro fastener on the bridge member that extends under the patient's neck. In use, the rigidity provided by the bridge member, as it is held in a fixed position by the fasteners, provides support for the chin-supporting portion of the collar. This rigid support is provided independently of the angular setting of the collar.

Figure 6:
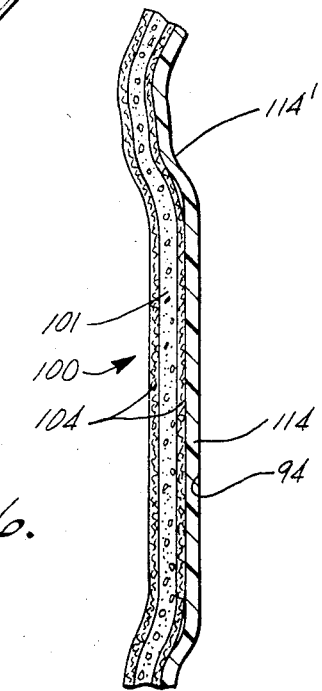
FIG. 6 is a fragmented cross-sectional view taken on line 6—6 of FIG. 5.

FIGS. 4 through 6 show an alternate cervical collar according to principles of this invention. This embodiment includes a generally U-shaped fixed front half 86 for supporting the chin region of a patient. A generally U-shaped rear half of the collar is not shown, but is similar to the rear half 12 shown in FIG. 1. The front half 86 of the collar is in the form of a thin three-dimensional shell having a chin-supporting upper section 88 and a lower section 90 that fits around and close to the front portion of the patient's neck and rests on the upper chest region of the patient. The shell is made from a single piece of a semi-rigid, self-supporting thin sheet-like material preformed to conform to the anatomical shape that can simultaneously support the underside of the chin region while fitting close to the front of the neck and be stabilized for support on the upper chest region. The shell is preferably made from a thin sheet of polyethylene that is sufficiently flexible to be vacuum-formed into the desired three-dimensional shape and which remains reasonably flexible after shaping.

The chin-supporting section 88 of the shell is an elongated upwardly opening U-shaped portion for extending under and along the sides of the patient's chin and for extending along and adjacent to the sides of the patient's jaw. The chin-supporting portion of the shell extends to rear portions 92 for overlying the rear portions of the patient's lower jaw.

The lower section 90 of the shell has a neck region 94 that conforms to the contour of the front portion of the patient's neck. The region of the shell extends downwardly generally normal to the chin and jaw-supporting portions 88 of the shell. The lower section of the shell extends downwardly below the neck region 94 to form a lower supporting portion 96 shaped to conform to the front portion of the collarbone and the upper central region of the patient's chest. Recessed slots 98 extending inwardly from opposite sides of the lower section of the shell are in a location that overlies the collarbone when the cervical collar is in use.

A layer 100 of padding covers the inside face of the shell. The layer of padding is similar to the padding used in the cervical collar described in FIGS. 1 through 3. That is, the padding comprises an internal layer of an open cell resilient plastic foam material 102 such as polyurethane foam. The open cell foam material is used because it is capable of breathing to allow air circulation through the cells and to absorb moisture. This allows heat dissipation during use.

The open cell foam layer is enclosed within an outer layer 104 of a soft flexible fabric that is also capable of breathing and is comfortable when in direct contact with the skin for prolonged time periods. The preferred material is velour. The enclosure formed by the velour is stitched around the outer perimeter of the foam layer and the resulting padding is then affixed to the inside face of the shell by a suitable adhesive. The padding covers the entire inside face of the shell and protrudes outwardly from the shell around its entire outer perimeter. Large exposed portions 106 of the foam padding overlie the collarbone in the recessed region 98 of the collar.

A narrow elongated upright reinforcing bar 108 extends vertically along the center of the lower front portion of the shell. The reinforcing bar is on the underside of the shell, under a vertical embossment or raised (inverted recessed) region 110 that conforms to the long narrow shape of the bar. Fasteners 112 affix the upper and lower ends of the bar to the shell. The reinforcing bar is preferably made from a metal that is sufficiently rigid to hold its shape during use, but which can be bent to allow the charging of the contour to better fit the patient. A preferable material is aluminum.

An elongated raised section in the form of a generally rectangular embossment 114 extends across the portion of the shell that overlies the neck region. The upper edge 114' of the raised embossed region extends along the top of the neck region 94 of the shell, immediately below where the chin-supporting region 88 flares outwardly from the neck region 94 of the shell. The embossment extends for essentially all of the length and height of the neck region 94. As shown in FIG. 6, the embossment is preformed into the shell wall without added reinforcing materials being used in the neck region. The raised form of the embossment is best shown in FIG. 6. The embossed region 114 provides reinforcing in the form of substantially increased resistance to collapsing under a vertical force when compared with a shell in the same shape not having the embossed region. The added stiffness is sufficient to prevent the neck region of the shell from collapsing under downward forces on the chin-supporting section that are normally encountered during use of the cervical collar.

An elongated layer 116 of a thistle cloth fastener material is affixed to the embossed neck region 114 of the shell. Preferably, the fastener material is a Velcro pile-type material. The layer of fastener material is preferably affixed to the front face of the shell by a suitable adhesive. The layer 116 is shown in phantom lines so the embossment can be shown.

In use, the front and rear halves of the cervical collar of FIGS. 4 through 6 can be attached to one another by extending the free ends of straps on the rear half over the layer of fastener material on the front half and attaching the cooperating Velcro surfaces to hold the front and rear halves of the collar in place in a manner similar to the front and rear halves of the collar described in FIGS. 1 through 3.

The front half of the cervical collar is used by placing the chin-supporting upper section 88 of the collar under the patient's chin, supporting it by resting the lower section 90 of the collar over the collarbone and the upper portion of the patient's chest region. The rear half of the cervical collar is then placed under the rear of the patient's head, and the straps are attached to the Velcro layer at the front of the cervical collar for holding the collar in place around the patient's neck. The reinforcing bar 108 is bent, prior to fitting the collar to the necessary anatomical shape so the inside face of the collar closely fits the patient. The neck region 94 of the collar fits closely around the front of the patient's neck, and this portion of the collar has sufficient stiffness to provide the vertical rigidity that gives the collar stability during use. The stiffness provided by the reinforced neck region of the collar is sufficient to resist normal downward forces on the chin support during use to maintain the chin-supporting section stable in supporting the underside of the chin. The shell provides all the support necessary for maintaining collar stability during normal use. The padding that covers the inside face of the collar is not self-supporting in and of itself; and therefore, it provides no additional stability. The shell thus provides all the required support as a one-piece, anatomically shaped and preformed self-supporting structure. During periods of prolonged use, the open cell foam padding is in contact with the patient. Since the open cell foam padding allows the padded portions of the collar to breathe, the collar is comfortable for the patient during long periods of use. The recessed regions of the collar that overlie the collarbone relieve pressure over the clavicular prominence for additional long-term comfort.

What is claimed is:

1. A cervical collar having an improved chin and lower jaw support, comprising:
   a self-supporting shell preformed as a single piece of thin, semi-rigid material shaped to conform to the anatomical contour of the underside of the chin and lower jaw, the front portion of the neck, and the upper chest region; reinforcing means comprising an embossed region of the shell extending across the length of the neck region of the shell for increasing the stiffness of the neck region of the shell without increasing the wall thickness of the shell to resist, without collapse, downward forces on the chin and lower jaw-supporting section of the shell normally encountered to use; and a layer of an open cell containing material on the inside face of the shell.

2. Apparatus according to claim 1, in which the embossed region extends for most of the length and most of the height of the neck region of the shell.

3. Apparatus according to claim 2, including an upright reinforcing bar extending along the central portion of the neck region and the upper chest region of the shell.

4. Apparatus according to claim 1, in which the open cell containing material is embedded between the shell and an outer layer of a porous, flexible material.

5. Apparatus according to claim 1, including a pair of opposed recessed regions in the collarbone region of the shell for overlying the clavicular prominences.

6. A cervical collar having an improved chin and lower jaw support, comprising:
   a self-supporting shell preformed as a single piece of a thin semi-rigid material shaped to conform to the anatomical contour of the underside of the chin and lower jaw, the front portion of the neck, and the upper chest region;
   reinforcing means comprising an embossed region of the shell extending across the length of the neck region of the shell for increasing the stiffness of the neck region of the shell without increasing the wall thickness of the shell to resist, without collapse, downward forces on the chin and lower jaw-supporting section of the shell normally encountered during use;
   an elongated upright reinforcing bar extending alobg the central portion of the neck region to the upper chest region of the shell;
   a pair of opposed recesses extending into the collarbone region of the shell for overlying the clavicular prominences; and a layer of an open cell containing material on the inside face of the shell.

7. A cervical collar having an improved chin and lower jaw support, comprising: a self-supporting shell preformed as a single piece of thin, semi-rigid material shaped to conform to the anatomical contour of the underside of the chin and lower jaw, the front portion of the neck, and the upper chest region; reinforcing means comprising an embossed region of the shell extending across the length of the neck region of the shell for increasing the stiffness of the neck region of the shell to resist, without collapse, downward forces on the chin and lower jaw-supporting section of the shell normally encountered during use; a layer of padding on the inside face of the shell; and means for holding the shell in a fixed position to support the chin and lower jaw.

8. Apparatus according to claim 7 in which the embossed region provides reinforcing in the form of substantially increased resistance to collapse under a vertical force when compared with the shell in the same shape not having the embossed region.

9. Apparatus according to claim 7 in which the embossment is an elongated raised section of the shell extending across a front face of the neck region of the shell immediately below the chin and lower jaw-supporting portion of the shell, and in which the embossed region extends for a height of the neck region of the shell substantially similar to the height of the portion of the shell overlying the neck region of the user.

* * * * *